US008770006B2

United States Patent
Harper

(10) Patent No.: US 8,770,006 B2
(45) Date of Patent: Jul. 8, 2014

(54) COMPOUND HINGED ROD BENDER

(75) Inventor: Michael Harper, Pottstown, PA (US)

(73) Assignee: Globus Medical, Inc., Audubon, PA (US)

( * ) Notice: Subject to any disclaimer, the term of this patent is extended or adjusted under 35 U.S.C. 154(b) by 40 days.

(21) Appl. No.: 13/219,295

(22) Filed: Aug. 26, 2011

(65) Prior Publication Data

US 2012/0047980 A1 Mar. 1, 2012

Related U.S. Application Data

(60) Provisional application No. 61/377,343, filed on Aug. 26, 2010.

(51) Int. Cl.
*B25B 7/00* (2006.01)
*B25B 7/12* (2006.01)

(52) U.S. Cl.
USPC ..................................... 72/409.01; 72/409.11

(58) Field of Classification Search
USPC ................. 72/409.01, 409.1, 409.11, 409.19, 72/409.16, 458; 81/349, 350, 351, 383.5, 81/416, 420
See application file for complete search history.

(56) References Cited

U.S. PATENT DOCUMENTS

| | | | | |
|---|---|---|---|---|
| 3,704,620 A | * | 12/1972 | Allen | 72/409.01 |
| 3,747,648 A | * | 7/1973 | Bauer | 72/409.01 |
| 4,474,046 A | * | 10/1984 | Cook | 72/409.16 |
| 5,490,409 A | * | 2/1996 | Weber | 72/409.1 |
| 5,536,270 A | * | 7/1996 | Songer et al. | 81/420 |
| 5,819,580 A | * | 10/1998 | Gauthier | 72/409.1 |
| 6,006,581 A | * | 12/1999 | Holmes | 72/409.1 |
| 6,325,432 B1 | * | 12/2001 | Sensat | 294/16 |

* cited by examiner

*Primary Examiner* — Teresa M Ekiert

(57) ABSTRACT

A compound rod bender includes a first handle arm and a second handle arm coupled to a first pivot point. A body portion of the rod bender is coupled to the first handle arm at a second pivot point and the second handle arm is coupled to the body portion at a third pivot point. The body portion also includes first and second distal arms configured with first and second rolling elements coupled to distal ends of the first and second distal arms. A barrel is provided on the body portion which is positioned on a center area of the body portion.

13 Claims, 4 Drawing Sheets

COMPOUND HINGED ROD BENDER

CROSS-REFERENCE TO RELATED APPLICATIONS

The present application is a non-provisional application which claims priority to provisional application Ser. No. 61/377,343 filed on Aug. 26, 2010, which is incorporated entirely herein.

FIELD OF THE INVENTION

The present disclosure generally relates to a device for bending elongated spinal rods and plates.

BACKGROUND

Bones and bony structures are susceptible to a variety of weaknesses that can affect their ability to provide support and structure. Weaknesses in bony structures may have many causes, including degenerative diseases, tumors, fractures, and dislocations. Advances in medicine and engineering have provided doctors with a plurality of devices and techniques for alleviating or curing these weaknesses. Typically, weaknesses in the spine are corrected by using devises that fuse one or more vertebrae together. Devices such as rods and plates are utilized to stabilize adjacent vertebrae. However, these rods and plates need to be bent or modified to accommodate the anatomy. Therefore, there is a need for a device which allows a surgeon to easily and accurately bend spinal rods and plates prior to insertion in to the body.

SUMMARY OF THE INVENTION

The present invention discloses a compound rod bender having a first handle arm and a second handle arm coupled to each other at a first pivot point. A body portion is coupled to the first handle arm at a second pivot point and the second handle arm is coupled to a third pivot point. The body portion includes a first and a second distal arm that are configured with first and second rolling elements which are coupled to the distal ends of the first and second distal arms. There is also provided a barrel positioned on a center portion of the body portion. A spinal rod is positionable between the first and second rolling elements and the barrel for bending when the first and second handle arms are actuated.

BRIEF DESCRIPTION OF THE DRAWINGS

The accompanying drawings, which are included to provide a further understanding of the disclosure, are incorporated in and constitute a part of this specification, illustrate aspects of the disclosure and together with the detailed description serve to explain the principles of the disclosure. No attempt is made to show structural details of the disclosure in more detail than may be necessary for a fundamental understanding of the disclosure and the various ways in which it may be practiced.

DETAILED DESCRIPTION OF THE INVENTION

While it is apparent that the invention disclosed herein is well calculated to fulfill the objects stated above, it will be appreciated that numerous modifications and embodiments may be devised by those skilled in the art.

Figure 1:
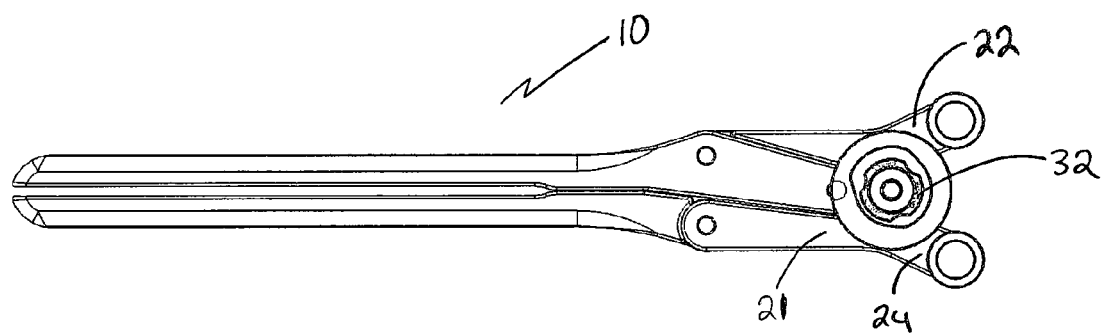
FIG. 1 is a compound rod bender according to the present invention in a closed position.
Figure 2:
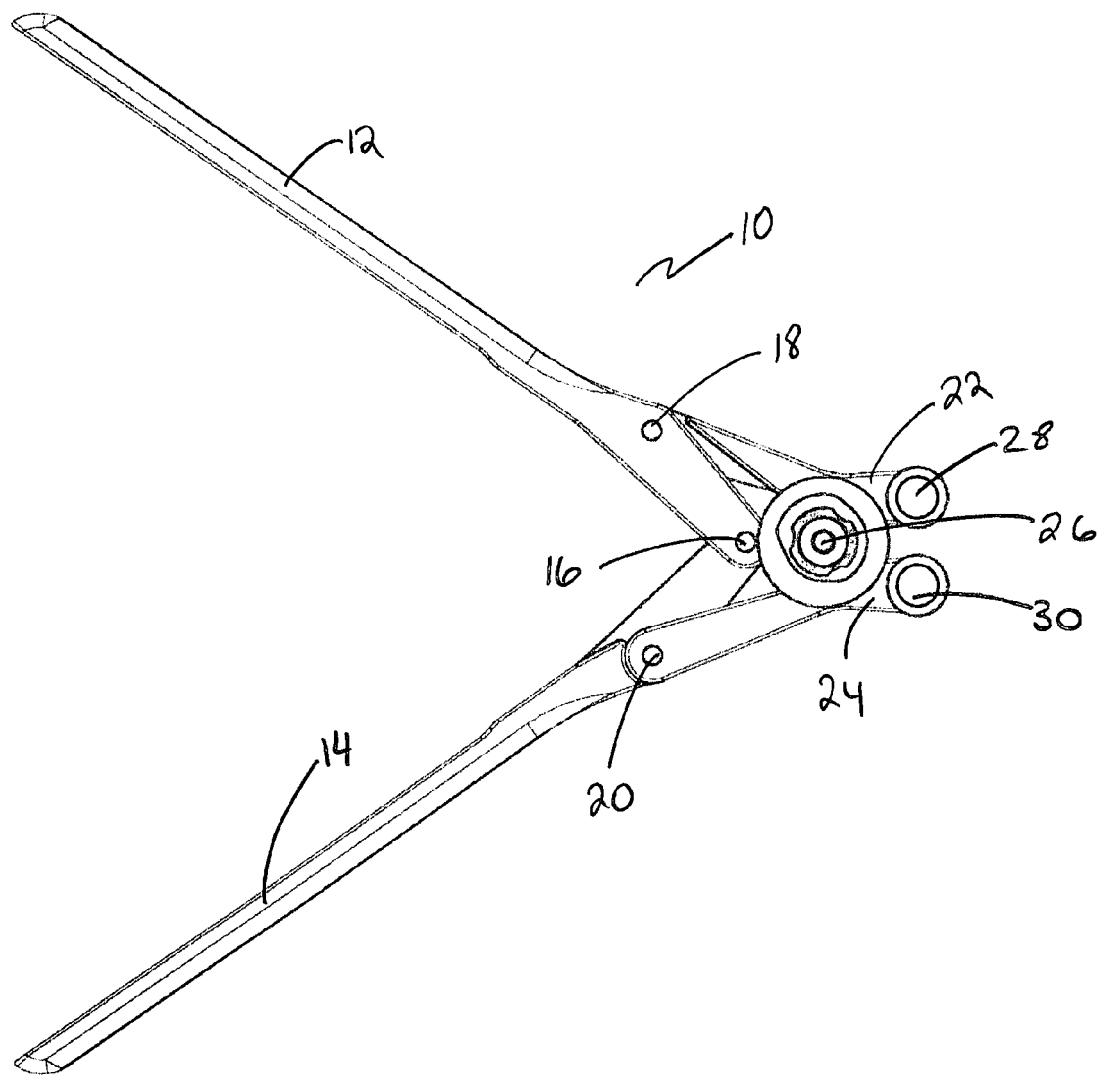
FIG. 2 is a compound rod bender according to the present invention in an open position.
Figure 3:
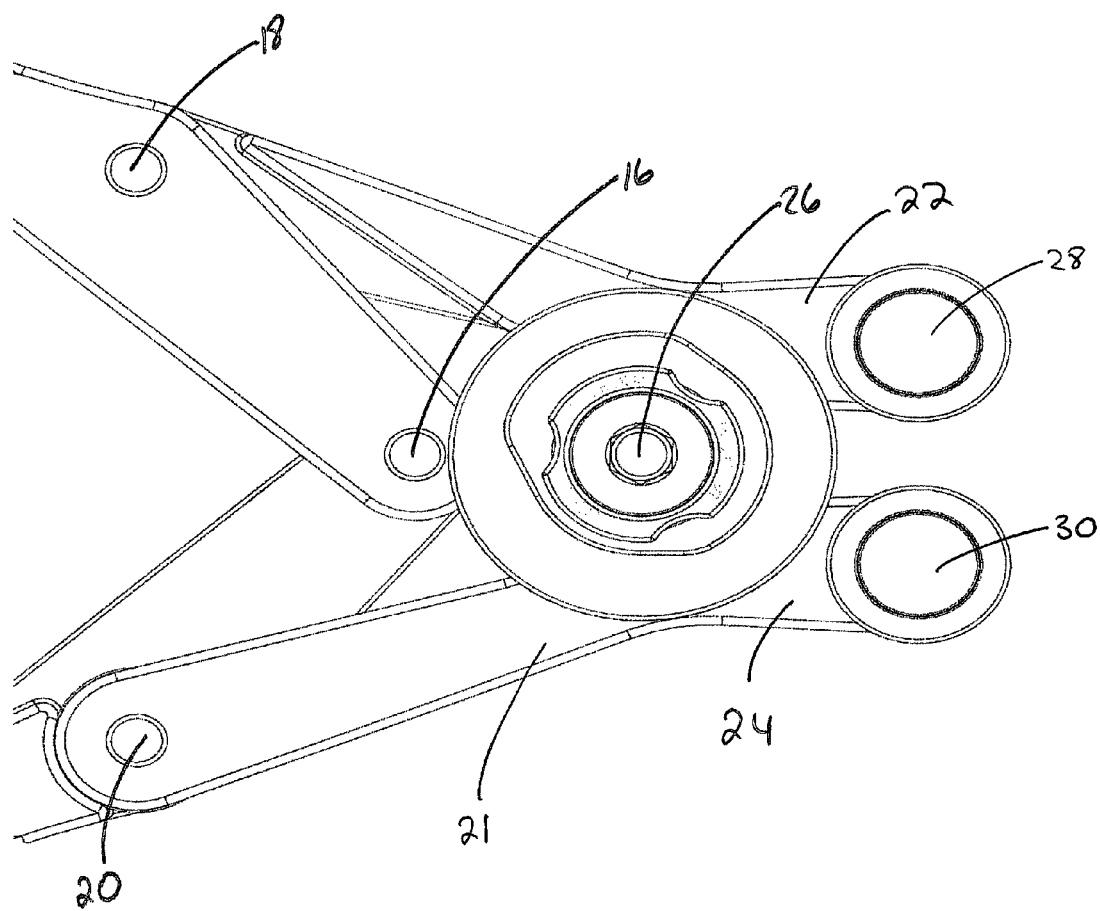
FIG. 3 is a top view of the body portion of the compound rod bender according to the present invention.
Figure 4:
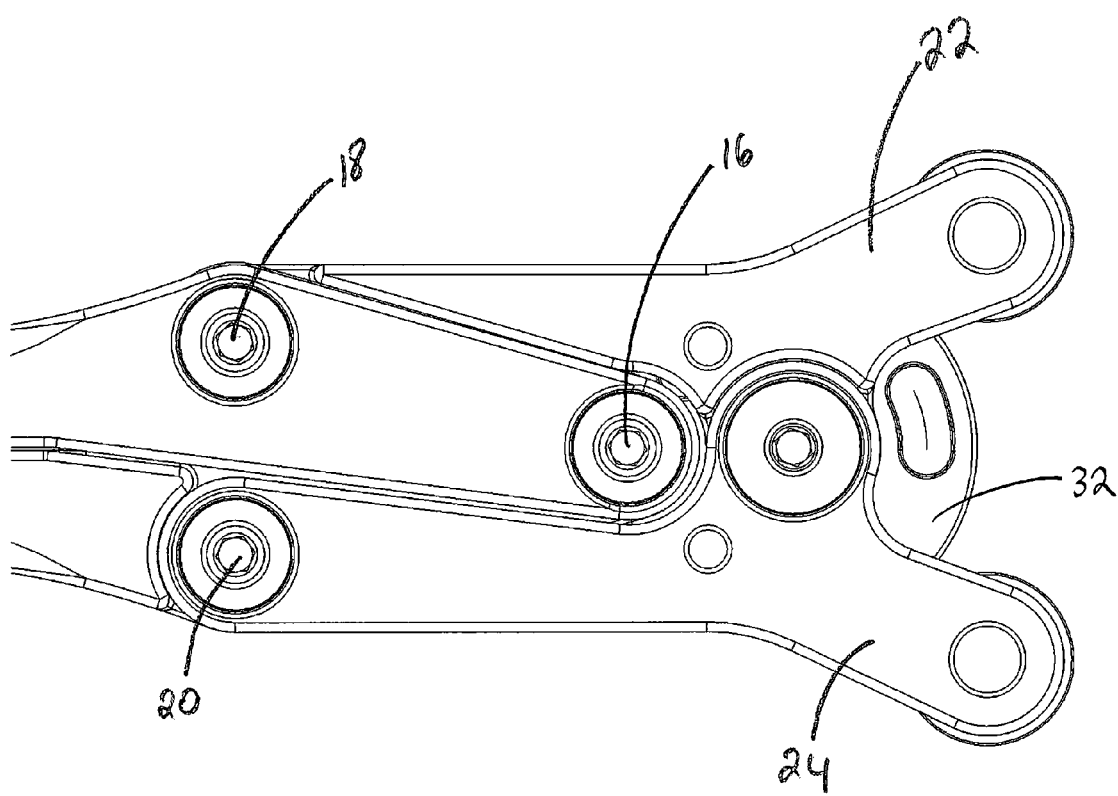
FIG. 4 is a bottom view of the body portion of the compound rod bender in a closed position according to the present invention.
Figure 5:
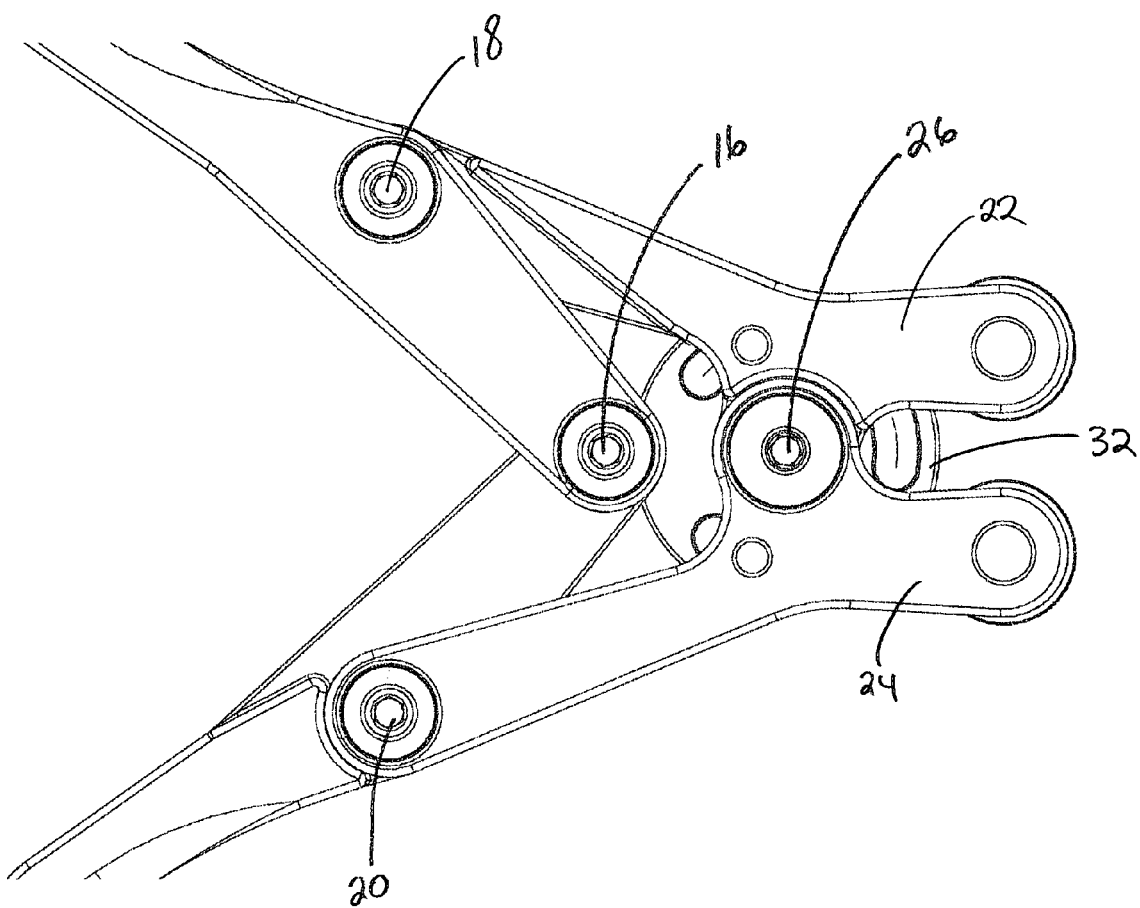
FIG. 5 is a bottom view of the compound rod bender in an open position according to the present invention.

FIGS. 1 and 2 illustrate a compound rod bender 10 in a closed position and in an open position. FIGS. 3-5 illustrate a top view and the bottom view of the rod bender in greater detail. Turning to FIGS. 1-5, the rod bender 10 comprises a first handle arm 12 and a second handle arm 14 that are coupled at a pivot point 16 and pivot points 18 and 20. The first handle arm 12 and the second handle arm 14 are connected to the body 21 of the compound rod bender 10 at pivot points 18 and 20, respectively. The rod bender 10 also comprises a first distal arm 22 and a second distal arm 24 which are configured about pivot point 26. The body 21 of the rod bender 10 is further provided with a first rolling element 28 and a second rolling element 30. The first rolling element 28 is positioned on the distal end of the first distal arm 22 and is configured to be rotatable. The second rolling element 30 is positioned on the distal end of the second distal arm 24 and is configured to be rotatable. The body 21 20 further provides a rotatable barrel 32 positioned below the first and second rolling elements 28 and 30. The rolling elements 28 and 30 are configured with rotating outer bearing portions which are substantially circular which are coupled to the first and second distal arms by a pin.

The barrel 32 is provided to support a rod when the rod is positioned between the rolling elements and the distal end of the barrel 32. The barrel 32 which is positioned on the pivot point 26 acts as a hinge between the two distal arms 22 and 24. The base portion of the barrel 32 includes a plurality of bending surfaces. Each bending surface can be selectively positioned into the desired operating position. The variety of bending surface contours enables the rod bender to accommodate different size rods, as well as provides for varying severities or contours of bend to the rod. The barrel 32 can be selectively rotated to cause the desired bending surface to be in appropriate position. During the operation of the rod bender 10, when the first and second handle arms 12 and 14 are actuated, a rod that is positioned in the rod bender is bent to accommodate the surgeon's preference. The radius of the bend in the rod can be manipulated by turning the barrel to various positions, as the circumference of the barrel is configured with different radii.

The rod bender of the present invention is operated as follows: First, the desired bending surface on the barrel is rotated and engaged into the operating position. The selected surface of the barrel faces toward the distal end of the instrument and operator positions a spinal rod between the rolling elements and the barrel after the handle arms of the instrument are moderately separated. This causes the distal arms to rotate in an arc upward and inward providing vertical clearance between the two distal arms and the barrel. After clearance is obtained, a suitable rod is then placed onto the selected bending surface of the barrel and the under the first and second rolling elements. A slight grip by the hands of the user will bring the distal arms and the rolling elements down and against the rod trapping it against the bending surface of the barrel. Additional force will bend the rod around the bending surface of the barrel. If a more or less severe bend is desired, the barrel can be rotated so that difference bending surface can be used.

The present invention includes the use of a compound hinge to increase the instruments mechanical advantage. The introduction of three additional pivot points and two lever arms will increase the instrument's output force dramatically, reducing the force required to contour a surgical rod when compared to a traditional rod bender. The relationship between the two sets of lever arms is directly related to the instrument's output force. It uses a compound joint to increase the bending force.

The various features and embodiments of the invention described herein may be used interchangeably with other feature and embodiments. Finally, while it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments which come within the spirit and scope of the present invention.

The invention claimed is:

1. A compound rod bender comprising:
   a first handle arm and a second handle arm coupled to a first pivot point;
   a body portion coupled to the first handle arm at a second pivot point and the second handle arm coupled to the body portion at a third pivot point,
   wherein the body portion comprises first and second distal arms configured with a first and second rolling elements coupled to distal ends of the first and second distal arms, and the body portion configured with a barrel positioned on a center portion of the body portion,
   wherein the barrel is rotatable and may be translated on the body portion into different positions for accommodating varying rod diameters.

2. The compound rod bender of claim 1, wherein the first and second rolling elements are rotatable.

3. The compound rod bender of claim 1, wherein the barrel is configured with a plurality of bending surfaces.

4. The compound rod bender of claim 1, wherein first and second handle arms are configured to pivot with respect to each other.

5. The compound rod bender of claim 1, wherein the first and second rolling elements are configured for conforming to the radius of the rod.

6. A spinal rod bending system comprising:
   an elongated spinal rod;
   a compound rod bender for manipulating an elongated spinal rod comprising:
   a first handle arm and a second handle arm coupled to each other at a first pivot point;
   a body portion coupled to the first handle arm and the second handle arm at second and third pivot points,
   wherein the body portion comprises first and second distal arms configured with first and second rolling elements coupled to distal ends of the first and second distal arms, and the body portion configured with a barrel positioned on a center portion,
   wherein the barrel is rotatable and may be translated on the body portion into different positions for accommodating varying rod diameters.

7. The system of claim 6, wherein the first and second rolling elements are rotatable.

8. The system of claim 6, wherein the barrel is configured with a plurality of bending surfaces.

9. The system of claim 6, wherein first and second handle arms are welded to each other at the first pivot point.

10. The system of claim 6, wherein the first and second rolling elements are configured for conforming to the radius of the rod.

11. A method for manipulating a spinal rod comprising:
    providing a compound rod bender, the compound rod bender comprising:
    a first handle arm and a second handle arm coupled to each other at a first pivot point;
    a body portion coupled to the first handle arm and the second handle arm at a second and third pivot point,
    wherein the body portion comprises first and second distal arms configured with first and second rolling elements coupled to distal ends of the first and second distal arms, and the body portion configured with a barrel positioned on a center portion of the body portion,
    positioning the spinal rod between the rolling elements and the barrel of the compound rod bender;
    actuating the first and second handle arms thereby bending the spinal rod; and
    rotating and translating the barrel into different positions for accommodating varying rod diameters.

12. The method of claim 11, wherein the first and second rolling elements are rotatable.

13. The method of claim 11, further comprising the step of pivoting the first and second handle arms with respect to each other at the first pivot point.

\* \* \* \* \*